United States Patent [19]

Yee et al.

[11] Patent Number: 5,202,260

[45] Date of Patent: Apr. 13, 1993

[54] **RESOLUTION OF α-TERTIARY CARBOXYLIC ACID ESTERS USING LIPASE FROM *CANDIDA LIPOLYTICA***

[75] Inventors: Christopher Yee, Needham; Todd A. Blythe, Boston; Alan E. Walts, Reading, all of Mass.

[73] Assignee: Genzyme Corporation, Cambridge, Mass.

[21] Appl. No.: 697,152

[22] Filed: May 8, 1991

[51] Int. Cl.⁵ .................................................. C12P 7/40
[52] U.S. Cl. ..................................... 435/280; 435/136
[58] Field of Search ................................ 435/280, 136

[56] References Cited

U.S. PATENT DOCUMENTS

| | | | |
|---|---|---|---|
| 3,405,159 | 10/1968 | Krieger et al. | 260/46 S |
| 3,830,827 | 8/1974 | Karady et al. | 280/471 |
| 3,895,052 | 7/1975 | Karady et al. | 260/471 A |
| 4,668,628 | 4/1987 | Dahod et al. | 435/135 |

OTHER PUBLICATIONS

Chenault, H. K. et al., *J. Am. Chem. Soc.* 111:6354–6364 (1989).
Kato Y, Tetrahed. Lett. 28:1303–06 (1987).
Sugai, T. et al, J. Org. Chem. 55:4643–4647 (1990).
Christen, M. et al, J. Chem. Soc. Commun 264–266 (1988).

*Primary Examiner*—Douglas W. Robinson
*Assistant Examiner*—S. Saucier

[57] ABSTRACT

A method for the resolution of α-tertiary carboxylic acid esters by partial hydrolysis is disclosed. The partial hydrolysis is carried out by contacting the esters with an aqueous solution in the presence of a lipase derived from *Candida lipolytica*, and the hydrolysis product is separated from unreacted starting material to obtain the hydrolysis product or the unreacted starting material in enantiomerically enriched form.

18 Claims, No Drawings

RESOLUTION OF α-TERTIARY CARBOXYLIC ACID ESTERS USING LIPASE FROM CANDIDA LIPOLYTICA

BACKGROUND OF THE INVENTION

The present invention relates to a method for preparing optically active acids and their corresponding esters by partial enzymatic hydrolysis of α-tertiary carboxylic acid esters using an enzyme derived from *Candida lipolytica*. The method of this invention is useful in preparing compounds which have utility as starting materials and intermediates for the synthesis of pharmaceuticals, and agricultural and veterinary products.

Review articles on enzymatic synthesis, such as D. H. G. Crout and M. Christen, *Modern Synthetic Methods*, 1989, vol. 5, R. Scheffold (Ed.), Springer-Verlag, and J. B. Jones, *Tetrahedron*, 1986, 42, 3351, describe many examples of the enzymatic resolution of esters in which the α-carbon possesses one hydrogen. However, relatively little has been reported for the enzymatic resolution of carboxylic acids or esters in which the α-carbon is fully substituted with moieties other than hydrogen.

Chenault et al., *J. Am. Chem. Soc.*, 1989, 111, 6354 describe the resolution of eight 2-amino-2-methyl carboxylic acids by partial hydrolysis of the amide moieties of racemic 2-N-acylamino-2-methyl carboxylic acids with acylase I from porcine kidney and from the fungus Aspergillus species. The enzymes display (S)-stereoselectivity, and three of the L-2-methylamino acids were prepared in greater than 90% enantiomeric excess. Results of the resolution of the N-acylmethyldopa derivative were not disclosed. The reported enzymatic resolutions require as much as twice the weight of enzyme to substrate and about eleven days to achieve 50% hydrolysis, and are therefore limited in their applications and in their usefulness in commercial processes.

Sugai et al., *J. Org. Chem.*, 1990, 55, 4643, describe the resolution of the racemic methyl ester of 2-benzyloxy-2-methyl-4-pentenoic acid (an α-oxygen substituted ester) to yield the optically pure (S)-acid which was subsequently used in the synthesis of (1S,5R)-(−)-frontalin, a constituent of the aggregation pheromone of the female southern pine bark beetle. The enantiomerically pure (S)-acid was obtained by enzymatically hydrolysing the racemic ester with *Candida cylindracea* lipase, isolating and then re-esterifying the enantiomerically enriched (S)-acid, and resubmitting the optically enriched (S)-ester to *Candida cylindracea* lipase hydrolysis. This sequence for preparing (S)-2-benzyloxy-2-methyl-4-pentenoic acid requires two enzymatic resolution steps which result in longer overall reaction times and lower chemical yields than a process which employs only one enzymatic resolution step.

Enzymatic resolution of α-tertiary 2-hydrazino-2-methyl carboxylic acid esters has not previously been reported in the literature. Such compounds are useful in the production of amino acid decarboxylase inhibitors, and in particular carbidopa, which is used in the treatment of Parkinson's disease. The current methods of production of compounds such as carbidopa employ chemical resolution of 2-hydrazino (U.S. Pat. No. 3,895,052) or 2-amino (U.S. Pat. No. 3,405,159) precursors. Such methods require expensive chiral auxiliaries or costly and complicated equipment. See also U.S. Pat. No. 3,830,827, which describes a chemical method for preparing carbidopa.

SUMMARY OF THE INVENTION

We have discovered that the enzyme obtained from *Candida lipolytica* is effective in resolving a variety of α-tertiary carboxylic acid esters of general formula

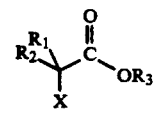

wherein $R_1$ and $R_2$ independently represent alkyl, substituted alkyl, alkenyl, substituted alkenyl, alkynyl, substituted alkynyl, aryl, substituted aryl, arylalkyl or substituted arylalkyl, or $R_1$ and $R_2$ together are linked to form a cyclic structure incorporating the asymmetric α-carbon atom; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; and X represents alkyl, substituted alkyl, halogen, amino, alkylamino, arylalkylamino, acylamino, hydrazino, alkylhydrazino, arylalkylhydrazino, arylhydrazino, acylhydrazino, hydroxyl, alkoxy, arylalkoxy, aryloxy, mercapto, alkylthio, arylalkylthio or arylthio; provided that $R_1$, $R_2$ and X are different from each other. The enzyme from *Candida lipolytica* has now been found to hydrolyze with high selectivity one isomer of a mixture of enantiomers of α-tertiary carboxylic acid esters. The resolution of these esters is accomplished by the partial hydrolysis of a solution or suspension of the ester in a predominantly aqueous mixture in the presence of the enzyme derived from *Candida lipolytica*, and separating the product acid from the starting ester. Separation is advantageously accomplished by methods well known to skilled practitioners of this art, such as by extraction, chromatography and selective precipitation. The selectivity of the present method permits the hydrolysis of predominantly one enantiomer, and preferably only one enantiomer.

In one aspect, the method of this invention can be applied to the enzymatic resolution of 2-hydrazino and 2-(β-N-acylhydrazino) esters, and in particular, alkyl 2-hydrazino-2-methyl-3-(4-hydroxy-3-methoxyphenyl)propionates and alkyl 2-(β-N-acylhydrazino)-2-methyl-3-(4-hydroxy-3-methoxyphenyl)propionates, the ester precursors of carbidopa. For the optical resolution of these esters, the method is carried out in aqueous medium, and the enzymatic reaction stops after the (S)-ester is hydrolyzed. The (S)-acid and (R)-ester can be conveniently separated, and the enantiomeric excess of each is at least about 99%.

In another aspect, the method of this invention can also be applied to the resolution of 2-amino-2-methyl carboxylic acid esters, such as alkyl 2-amino-2-methyl-3-(3,4-dihydroxyphenyl)propionate, which are precursors to the antihypertensive agent methyldopa. Enzymatic hydrolysis of the ester function of methyldopa esters affords (S)-methyldopa and the corresponding (R)-alkyl esters.

Other compounds which can be enzymatically resolved using the method of this invention include α-tertiary 2-hydroxy carboxylic acids such as racemic 2-benzyloxy-2-methyl-4-pentenoic acid.

The method of this invention is convenient, requires no costly or complicated equipment, and can be readily adopted for large-scale production of enantiomerically enriched α-tertiary carboxylic acids and their corresponding esters. The use of *Candida lipolytica* enzyme also has the advantages of greater hydrolytic activity and enantioselectivity than *Candida cylindracea* lipase with respect to the synthesis of 2-hydroxy-2-methyl or 2-alkoxy-2-methyl carboxylic acids, resulting in simplified and higher-yielding processes.

The compounds of this invention are useful as intermediates in the synthesis of pharmaceuticals, agricultural and veterinary products.

DESCRIPTION OF THE PREFERRED EMBODIMENTS

The chiral acids and their corresponding esters of this invention can be generally obtained as follows. A racemic carboxylic acid ester of the general formula

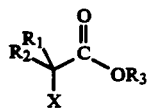

I wherein $R_1$ and $R_2$ independently represent alkyl, substituted alkyl, alkenyl, substituted alkenyl, alkynyl, substituted alkynyl, aryl, substituted aryl, arylalkyl or substituted arylalkyl, or $R_1$ and $R_2$ together are linked to form a cyclic structure incorporating the asymmetric α-carbon atom; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; and X represents alkyl, substituted alkyl, halogen, amino, alkylamino, arylalkylamino, acylamino, hydrazino, alkylhydrazino, arylalkylhydrazino, arylhydrazino, acylhydrazino, hydroxyl, alkoxy, arylalkoxy, aryloxy, mercapto, alkylthio, arylalkylthio or arylthio; provided that $R_1$, $R_2$ and X are different from each other, is dissolved or suspended in water or an aqueous buffer so that the final concentration of the substrate ranges from 0.001 to 6.0 moles per liter of reaction volume. The molarity of the buffer may range from 0.001 to 0.5M, but to facilitate the isolation of the product acid, water or 0.01 to 0.05M buffer is preferred. The concentration of the buffer may be increased or decreased for convenience in conducting the enzymatic hydrolysis or product isolation. The pH of the resulting solution or slurry is adjusted to between 4 and 8.5, but a pH range of 7 to 8 is preferred. The aqueous medium can also include up to about 75%, but preferably less than 15%, by volume of a miscible organic solvent, including but not limited to methanol, ethanol, 1-propanol, 2-propanol, acetone, 2-butanone, acetonitrile, dimethylformamide or dimethylsulfoxide. The use of a miscible organic solvent may serve to improve the solubility of certain substrates.

The enzyme is added to the substrate mixture to initiate the reaction and the resulting mixture is agitated. The optimum amount of enzyme used varies with the protein content of the enzyme preparation, the substrate and the reaction temperature, and a range of from 1 to 200 mg of protein per gram of substrate is preferred if crude enzyme is used. The optimum reaction temperature at which the hydrolysis is conducted may vary, and can range from 0° C. to 55° C., but 15° C. to 37° C. is preferred. The atmosphere above the reaction may be air, or an inert gas, such as nitrogen. If the reaction proceeds for more than two days or at elevated temperatures, an inert atmosphere is preferred.

The enzyme used in this invention is commercially available and is derived from the yeast *Candida lipolytica* which is also known as *Yarrowia lipolytica*. A particularly preferred *Candida lipolytica* enzyme for the purposes of this invention is that which is commercially available from Fluka Chemie AG, sold under the name "Lipase from *Candida lipolytica*". The commercial enzyme is actually believed to be a mixture of at least six discrete species as determined by polyacrylamide gel electrophoresis (PAGE), various salts and buffer components and the like, as well as water insoluble material.

The crude enzyme that is obtained from commercial suppliers may be used without modification in the resolution of the present substrates. Equally effective in resolving these substrates is the enzyme which has been partially purified by chromatographic methods. Purification can be carried out by various methods which are suitable for this purpose and known to those skilled in the art.

It has also been found that the crude or purified fractions of the enzyme can be immobilized on various solid supports without loss of stereospecificity or change in stereoselectivity. The solid supports can either be inert adsorbents to which the enzyme is not covalently bonded, but instead is adsorbed by any number of phenomena including, but not limited to, interactions of hydrophobic or hydrophilic portions of a protein with like regions of the inert adsorbent, by hydrogen bonding, by salt bridge formation, or by electrostatic interactions. Inert adsorbent materials include, but are not limited to, synthetic polymers (e.g. polystyrene, poly(vinylalcohol), polyethylene and polyamides), mineralaceous compounds (e.g. diatomaceous earth and Fuller's earth), or naturally occurring polymers (e.g. cellulose). Specific examples of such materials include Celite 545 diatomaceous earth, Amberlite XAD-8 polymeric resin beads and polyethylene glycol 8000. The enzyme may also be immobilized on supports to which the enzyme is covalently bonded (e.g. oxirane-acrylic beads and glutaraldehyde activated supports). Specific examples include Eupergit C oxirane-acrylic beads and glutaraldehyde activated Celite 545. Other possible immobilizing systems are well known and are readily available to those skilled in the art of enzyme immobilization. These immobilized enzyme preparations offer more predictable results, simplify reaction processes and product isolation, and reduce the cost of the enzyme.

The initial pH of the reaction mixture can be maintained by constant addition of an inorganic base such as sodium hydroxide, or by the use of a suitable buffer. The extent of hydrolysis is monitored by the amount of base added, or by periodic withdrawal of aliquots of the reaction mixture and measuring the relative amounts of starting material and product by high pressure liquid chromatography. For the purpose of making the optically active acid, the reaction may be terminated after 5% to 50% hydrolysis has occurred, but to maximize chemical yield, 40% to 50% hydrolysis is preferred.

The product is separated from the unreacted ester by adjusting the pH of the reaction mixture to 7.5–8, and extracting the ester with an organic solvent such as methylene chloride, ethyl acetate, diethyl ether, or other volatile solvent in which the substrate is stable and soluble, and which is also immiscible in the aqueous phase. Concentration of the organic extracts affords the unreacted ester, while concentration of the aqueous phase yields the acid which can be freed of buffer salts by selective precipitation or chromatography, or other methods known to those skilled in the art.

Alternatively, the reaction mixture may be acidified, e.g. to pH 3, and both the ester and acid extracted into organic solvents such as methylene chloride, ethyl acetate, diethyl ether, or any volatile solvent in which the substrate is stable, soluble and which is immiscible with the aqueous phase. Concentration of the organic extract yields a mixture of the ester and acid, and these may be separated by selective precipitation or chromatography, or by other methods known to those skilled in the art. Methods for determining the enantiomeric excess of the esters and the acids depend on the nature of the substituent X, and are illustrated by the examples that are described hereinafter.

The chiral esters are prepared by a method similar to that described for the preparation of the chiral acids. The difference is the hydrolysis is allowed to proceed to 50% to 95%, but in the interest of maximizing the chemical yield, 50% to 60% hydrolysis is preferred. Product separation and isolation is the same as described previously for the chiral acids.

The esters and acids may each also be prepared as described above using the purified enzyme instead of the crude enzyme. This purified enzyme offers more consistent results and easier isolation of products.

For the resolution of esters wherein X is NHNHY, and Y is H or COCH$_2$Ph, a solution or suspension of degassed water or sodium phosphate buffer containing from about 0.001 moles to about 2.0 moles of substrate per liter of reaction volume is adjusted to pH 7.5. A quantity of crude *Candida lipolytica* enzyme corresponding to 20 mg of protein per gram of substrate is added to initiate the reaction. The reaction mixture is placed under a nitrogen atmosphere and stirred at 36° C. The pH is maintained at 7.3–7.8 by continuous addition of sodium hydroxide until 50% hydrolysis is achieved. The unreacted ester is removed by extraction with methylene chloride, then concentrated in vacuo to afford the (R)-ester in greater than 98% enantiomeric excess. The aqueous phase is concentrated in vacuo to one tenth its original volume, diluted with three volumes of ethanol, adjusted to pH 6.5 with diethylamine, then aged at 0° C. to 5° C. for several hours to precipitate the (S)-acid. To measure the enantiomeric excess and confirm the absolute stereochemistry of the (R)-esters and (S)-acids, the compounds are converted, by acid hydrolysis, to the (R)- and (S)-3-(3,4-dihydroxyphenyl)-2-hydrazino-2-methylpropanoic acids, respectively. The hydrazino acids are then converted to their respective β-N-(1S)-camphanoyl derivatives and compared to similarly derivatized authentic reference standards by HPLC.

For the resolution of compounds wherein X represents NH$_2$, the methods described above can also be advantageously applied. The amino acids prepared in this manner are derivatized with 2,3,4,6-tetra-0-acetyl-B-D-glucopyranosyl isothiocyanate instead of (1S)-(−)-camphanoyl chloride, and the diastereomeric excess of the resulting thiourea is determined by HPLC.

The following examples further illustrate, but do not limit, the applications of this invention.

EXAMPLE 1

Preparation of (±)-butyl 2-hydrazino-2-methyl-3-(4-hydroxy-3-methoxyphenyl)-propionate To 100 mL of n-butanol saturated with hydrogen chloride gas at 0° C. to 5° C. is added 1.98g (8.2 mmol) of 2-hydrazino-2-methyl-3-(4-hydroxy-3-methoxyphenyl)propionic acid, and the resulting suspension is heated at reflux for 2h. The reaction mixture is then concentrated to dryness in vacuo. The residue is dissolved in sufficient saturated sodium bicarbonate solution to give a solution of pH 7.5–8. The product is extracted with chloroform, dried over magnesium sulfate and then concentrated in vacuo to afford 2.1 g (6.95 mmol, 84% yield) of the hydrazino acid ester. Recrystallization from a mixture of methylene chloride and hexane affords 1.96g (80% yield) of the product ester: mp 84.5° C. to 87.0° C.; HPLC analysis (C-18 column, 280 mm, $t_R$=16.2 min) showed a single peak; IR(CHCl$_3$ solution) 3540, 2860, 1720, 1515 cm$^{-1}$; $^1$H NMR (400 MHz, CDCl$_3$) δ 6.79 (d, 7.6 Hz, 1H), 6.62 (s, 1H), 6.59 (d, 7.6 Hz, 1H), 4.08 (m, 2H), 3.82 (s, 3H), 2.99 (d, 14 Hz, 1H), 2.74 (d, 14 Hz, 1H), 1.58 (m, 2H), 1.34 (m and s, 5H), 0.90 (t, 7.2 Hz, 3H).

EXAMPLE 2

Preparation of (±)-ethyl 2-hydrazino-2-methyl-3-(4-hydroxy-3-methoxyphenyl)-propionate The procedure of Example 1 is repeated with ethanol instead of n-butanol. The ethyl 2-hydrazino-2-methyl-3-(4-hydroxy-3-methoxyphenyl)propionate is obtained in 79% yield after recrystallization from acetonitrile: mp 114° C. to 116° C.; HPLC analysis (C-18 column, 280 nm, $t_R$=5.3 min) showed a single peak; IR (CHCl$_3$ solution) 3540, 2990, 2940, 1710, 1510 cm$^{-1}$; $^1$H-NMR (400 MHz, CDCl$_3$) δ 6.79 (d, 7.6 Hz, 1H), 6.63 (s, 1H), 6.60 (d, 7.6 Hz, 1H), 4.14 (q, 7.1 Hz, 2H), 3.83 (s, 3H), 2.99 (d, 13.5 Hz, 1H), 2.74 (d, 13.5 Hz, 1H), 1.34 (s, 3H), 1.24 (t, 7.1 Hz, 3H).

EXAMPLE 3

Preparation of (±)-butyl 2-amino-2-methyl-3-(3,4-dihydroxyphenyl)propionate

The procedure of Example 1 is repeated employing 2-amino-2-methyl-3-(3,4-dihydroxyphenyl)propionic acid rather than 2-hydrazino-2-methyl-3-(4-hydroxy-3-methoxyphenyl)propionic acid. The (±)-butyl 2-amino-2-methyl-3-(3,4-dihydroxyphenyl)propionate is obtained in a yield of 82%. The product is recrystallized from acetonitrile (77% yield) to give pure ester: mp 121.5° C. to 122° C.; HPLC analysis (C-18 column, 280 nm, $t_R$=14.5 min) showed >99% purity.

EXAMPLE 4

Preparation of (±)-ethyl 2-(β-N-phenylacetylhydrazino)-2-methyl-3-(4-hydroxy-3-methoxyphenyl))propionate To a solution of ethyl 2-hydrazino-2-methyl-3-(4-hydroxy-3-methoxyphenyl)propionate (1.00g, 3.73 mmol) in 9.2 ml of tetrahydrofuran and 9.2 ml of 1,4-dioxane at 0° C. to 5° C. is added triethylamine (377.4 mg, 3.73 mmol) followed by dropwise addition of phenylacetyl chloride (576.7 mg, 3.73 mmol). The resulting suspension is stirred at room temperature for 2h and then concentrated to dryness in vacuo. Purification of this concentrated product by silica gel chromatography (55% hexane in ethyl acetate) yields 1.01 g (2.62 mmol, 70%) of the (±)-ethyl 2-(β-N-phenyl-acetylhydrazino)-2-methyl-3-(4-hydroxy-3-methoxyphenyl)propionate: HPLC analysis (C-18 column, 280 nm, $t_R$=17.6 min); IR (CCl$_4$ solution) 3050, 3300 (br), 2980, 1720, 1670, 1510 cm$^{-1}$.

EXAMPLE 5

Preparation of (R)-ethyl 2-(β-N-phenylacetylhydrazino-2-methyl-3-(4-hydroxy-3-methoxyphenyl)propionate and (S)-2-(β-N-phenylacetyl hydrazino)-2-methyl-3-(4-hydroxy-3-methoxy)propionic acid A solution of (±)-ethyl 2-(3-phenylacetyl)hydrazino-2-methyl-3-(4-hydroxy-3-methoxyphenyl)propionate (128.0 mg, 0.331 mmol) in 3.40 ml of ethanol is suspended in 43.0 ml of 50 mM sodium phosphate buffer (pH 7.5). Enzyme from Candida lipolytica (26 mg of protein) is added, and the resulting suspension is agitated at room temperature for 41 h, at which time 50% hydrolysis is observed. The reaction mixture is extracted with 3×50 ml of methylene chloride. The combined extracts are washed with water, dried over magnesium sulfate, then concentrated in vacuo to yield 55.3 mg (0.143 mmol) of (R)-ethyl 2-(β-N-phenylacetylhydrazino)-2-methyl-3-(4-hydroxy-3-methoxyphenyl)propionate (43.2%). The chemical purity by HPLC assay is >97%. (C-18 column, 280 nm, $t_R$=17.6 min), with no hydrazino acid present. To determine the enantiomeric purity of the unreacted ester, 5.4 mg of the (R)-ester is heated in a sealed tube with 300 μL of concentrated HCl at 120° C. for 2 h to give (R)-2-hydrazino-2-methyl-3-(3,4-dihydroxyphenyl)propionic acid. The resulting acid solution is concentrated to dryness in vacuo. The residue is then derivatized with (1S)-(−)-camphanic chloride using a modification of the method reported by Trimble and Vederas (L. A. Trimble and J. C. Vederas, J. Am. Chem. Soc., 1986, 108, 6397). HPLC: (C-18 column, 280 nm, (S,S)-diastereomer $t_R$=9.2 min, (R, S)-diastereomer $t_R$=11.7 min). The diastereomeric excess is found to be >99% and the (R,S)-stereochemistry of the hydrazide derivative is assigned by comparison to an identically derivatized sample of USP Reference Standard of (S)-2-hydrazino-2-methyl-3-(3,4-dihydroxyphenyl)propioinic acid.

The recovered aqueous layers containing the (S)-2-(β-N-phenylacetylhydrazino)-2-methyl-3-(4-hydroxy-3-methoxyphenyl)propionic acid are adjusted to pH 3 with 1N HCl and then extracted with 3×50 ml of methylene chloride. The combined extracts are dried over magnesium sulfate, followed by concentration in vacuo to afford the product. Purification by preparative HPLC affords 6.4 mg (17.9 umol) of (S)-2-(β-N-phenylacetyl hydrazino)-2-methyl-3-(3-methoxy-4-hydroxyphenyl)propionic acid (11% yield). The (S)-2-(β-N-phenylacetylhydrazino)-2-methyl-3-(4-hydroxy-3-hydroxyphenyl)propionic acid is hydrolysed to (S)-2-hydrazino-2-methyl-3-(3,4-dihydroxyphenyl) propionic acid and, then derivatized with (1S)-(−)-camphanic chloride as described above. The derivative is analysed by HPLC (C-18 column) and found to have (S,S) stereochemistry with the diastereomeric excess >99%.

EXAMPLE 6

Preparation of (S)-2-hydrazino-2-methyl-3-(4-hydroxy-3-methoxyphenyl)propionic acid To a solution of 1.2 g (4.1 mmol) of (±)-butyl 2-hydrazine-2-methyl-3-(4-hydroxy-3-methoxyphenyl) propionate in 1 L of sodium phosphate buffer (50 mM, pH 7.5) is added crude Candida lipolytica enzyme (12 mg of protein), and the resulting mixture is incubated in a heated orbit shaker (200 rpm) at 36° C. The reaction is terminated at 20.5% conversion after 17h. The unreacted, optically enriched (R)-butyl 2-hydrazino-2-methyl-3-(4-hydroxy-3-methoxyphenyl)propionate is removed via extraction with methylene chloride. Lyophilization of the remaining aqueous layer and purification of the resulting solid by preparative reverse phase HPLC affords the (S)-2-hydrazino-2-methyl-3-(4-hydroxy-3-methoxyphenyl)propionic acid in 7% yield. A portion of this product (5 mg) is dissolved in 5 mL of sodium phosphate buffer (0.5M, pH 7.5) and to the resulting solution is added (1S)-(−)-camphanic chloride (50mg in 1 mL of THF) to give the diastereomeric camphanic hydrazide. HPLC analysis of the hydrazide shows the (S,S)-diastereomer to be in >99% diastereomeric excess (C-18 column, 280 nm, (S,S)-diastereomer $t_R$=21.6 min, (R,R)-diastereomer $t_R$=26.4 min).

EXAMPLE 7

Preparation of (S)-2-hydrazino-2-methyl-3-(4-hydroxy-3-methoxyphenyl)propionic acid and (R)-butyl 2-hydrazino-2-methyl-3-(4-hydroxy-3-methoxyphenyl)-propionate using purified Candida lipolytica enzyme The procedure of Example 6 is repeated with 10.5 mg of the racemic butyl ester and 9.4 mg of purified Candida lipolytica enzyme in 2 mL of water. The resulting suspension is incubated at 36° C. in an orbit shaker (200 rpm). After 4.5 h, 48% of the ester is hydrolysed, and at 16 h, 50% hydrolysis of the ester is observed. The unreacted ester is extracted with methylene chloride and purified by preparative HPLC. The remaining aqueous layer is lyophilized and the residue purified by preparative HPLC. Analysis of the enantiomeric excess of the (R)-ester and (S)-acid via their diastereomeric (1S)-camphanic hydrazide derivatives, prepared as described in Example 5, show both are greater than 99%.

EXAMPLE 8

Preparation of (R)-ethyl 2-hydrazino-2-methyl-3-(4-hydroxy-3-methoxyphenyl)-propionate and (S)-2-hydrazino-2-methyl-3-(4-hydroxy-3-methoxyphenyl)propanoic acid The procedure of Example 6 is repeated employing (±)-ethyl 2-hydrazino-2-methyl-3-(4-hydroxy-3-methoxyphenyl)propionate rather than (±)-butyl 2-hydrazino-2-methyl-3-(4-hydroxy-3-methoxyphenyl) propionate. The enzymatic hydrolysis is allowed to proceed to 50% conversion and the unreacted ethyl ester is extracted with methylene chloride. A portion of the ester is hydrolysed in concentrated HCl, and then derivatized with (1S)-(−) camphanic chloride as described in Example 5. The camphanic hydrazide derivative was found to be the (R,S)-diastereomer, and the diastereomeric excess was >98%.

EXAMPLE 9

Resolution of (±)-ethyl 2-hydroxy-2-methyl-3-(4-hydroxy-3-methoxyphenyl)-propionic acid To a suspension of 109 mg (0.43 mmol) of (±)-ethyl 2-hydroxy-2-methyl-3-(4-hydroxy-3-methoxyphenyl)-propionic acid in 4.6 mL of sodium phosphate buffer (50 mM, pH 7.5) is added crude enzyme from *Candida lipolytica* (7 mg of protein), and the reaction mixture is stirred at 20° C. After 2.5 h, 50% conversion is observed by HPLC (C-18 column, 280 nm, acid $t_R=7$ min, ester $t_R=10.2$ min). The reaction mixture is diluted with 20 mL of $H_2O$ and the unreacted ester is extracted with ethyl acetate (2×25 mL). The combined extracts are washed with saturated sodium bicarbonate solution, dried ($MgSO_4$) and concentrated in vacuo to afford 27 mg of unreacted ester (HPLC shows one peak). The enantiomeric excess of the unreacted ester was determined by HPLC analysis (Chiracel OD column from J. T. Baker, 280 nm, first enantiomer $t_R=7$ min, second enantiomer $t_R=10.3$ min) to be >99% for the faster eluting enantiomer.

What is claimed is:

1. A method of separating the enantiomers of racemic carboxylic acid esters of general formula

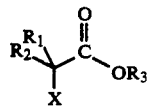

wherein $R_1$ represents alkyl, substituted alkyl, arylalkyl or substituted arylalkyl; $R_2$ represents alkyl or substituted alkyl; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; and X represents amino, alkylamino, arylalkylamino, acylamino, hydrazino, alkylhydrazino, arylalkylhydrazino, arylhydrazino, acylhydrazino, hydroxyl, or alkoxy, provided that $R_1$, $R_2$ and X are different from each other, by the enzymatic hydrolysis of one by the (S)-enantiomer of the ester, said method comprising contacting the racemic ester in an aqueous medium with an enzyme obtained from *Candida lipolytica* to hydrolyze from about 5% to about 95% of the ester, and separating the hydrolysis product from the unreacted starting material.

2. The method of claim 1 wherein the aqueous medium contains a buffer.

3. The method of claim 2 wherein the buffer is present in a concentration range of from about 1 to about 500 millimolar.

4. The method of claim 1 wherein the aqueous medium contains up to about 75% of an organic solvent.

5. The method of claim 4 wherein the organic solvent is selected from the group consisting of methanol, ethanol, 1-propanol, 2-propanol, acetonitrile, acetone, 2-butanone, dimethylformamide and dimethylsulfoxide.

6. The method of claim 1 wherein the hydrolysis product is separated from unreacted staring material by extraction with an organic solvent.

7. The method of claim 6 wherein the organic solvent is selected from the group consisting of methylene chloride, chloroform, tetrahydrofuran, t-butyl methyl ether, and ethyl acetate.

8. The method of claim 1 wherein the enzymatic hydrolysis is carried out at a temperature of from about 0° C. to about 55° C.

9. The method of claim 8 wherein the enzymatic hydrolysis carried out at a temperature of from about 15° C. to about 37° C.

10. The method of claim 1 wherein the enzyme is immobilized on a solid support.

11. The method of claim 1 wherein the enzyme is a purified fraction of a crude enzyme obtained from *Candida lipolytica*.

12. The method of claim 1 wherein X is selected from the group consisting of hydroxyl, amino, acylamino, hydrazino and acylhydrazino.

13. The method of claim 9 wherein X is selected from the group consisting of OH, $NHR_5$, and $NHNHR_5$; $R_5$ represents H, $COCH_3$ or $COCH_2Ph$; $R_3$ is $C_1$ to $C_8$ n-alkyl; $R_1$ is $CH_3$; and $R_2$ is represented by the formula

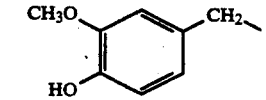

14. The method of claim 13 wherein $R_5$ is H.

15. The method of claim 14 wherein $R_3$ is butyl or ethyl.

16. The method of claim 13 wherein X is $NHR_5$.

17. The method of claim 13 wherein the hydrolyzed enantiomer is produced in at least about 95% enantiomeric excess.

18. The method of claim 12 wherein X is $OR_6$; $R_6$ is H or $OCH_2PH$; $R_3$ is $C_1$ to $C_8$ n-alkyl; $R_1$ is $CH_3$; and $R_2$ is allyl.

* * * * *

UNITED STATES PATENT AND TRADEMARK OFFICE
CERTIFICATE OF CORRECTION

PATENT NO. : 5,202,260
DATED : April 13, 1993
INVENTOR(S) : Christopher Yee, et al It is certified that error appears in the above-indentified patent and that said Letters Patent is hereby corrected as shown below:

Column 9, line 45, cancel "one by" and isnert therefor the word --only--.

Signed and Sealed this

Seventh Day of June, 1994

Attest:

BRUCE LEHMAN

*Attesting Officer*      *Commissioner of Patents and Trademarks*